US012745960B2

(12) United States Patent
Majerus et al.

(10) Patent No.: US 12,745,960 B2
(45) **Date of Patent: *Sep. 29, 2026**

(54) FLEXIBLE SENSOR APPARATUS AND METHOD OF MAKING SAME

(71) Applicants: Case Western Reserve University, Cleveland, OH (US); The United States as represented by the Department of Veterans Affairs, Washington, DC (US)

(72) Inventors: Steve Ja Majerus, University Heights, OH (US); Jeremy Dunning, Cleveland Heights, OH (US); Katherine M. Bogie, Cleveland, OH (US); Joseph A Potkay, Plymouth, MI (US)

( * ) Notice: Subject to any disclaimer, the term of this patent is extended or adjusted under 35 U.S.C. 154(b) by 63 days.

This patent is subject to a terminal disclaimer.

(21) Appl. No.: 18/743,201

(22) Filed: Jun. 14, 2024

(65) Prior Publication Data

US 2024/0324958 A1 Oct. 3, 2024

Related U.S. Application Data

(63) Continuation of application No. 18/108,808, filed on Feb. 13, 2023, now Pat. No. 12,036,042, which is a (Continued)

(51) Int. Cl.
*A61B 5/00* (2006.01)
*A61B 5/021* (2006.01)
(Continued)

(52) U.S. Cl.
CPC .......... *A61B 5/683* (2013.01); *A61B 5/02141* (2013.01); *A61B 5/02444* (2013.01);
(Continued)

(58) Field of Classification Search
CPC ... G01L 19/147; G01L 9/0042; G01L 9/0054; G01L 9/0072; G01L 13/025; G01L 19/04; G01L 19/0038; G01L 19/0084; G01L 19/14; G01L 9/0075; G01L 19/0069; G01L 19/0618; G01L 9/0055; G01L 9/0073; G01L 19/0092; G01L 19/0645; G01L 19/143; G01L 9/0051; G01L 9/0052; G01L 11/025; G01L 19/0007; G01L 19/0046;
(Continued)

(56) References Cited

U.S. PATENT DOCUMENTS 12,364,434 B2 * 7/2025 Majerus ............... A61B 5/6876
2015/0216476 A1 * 8/2015 Demir ................. A61B 5/4504
600/587

(Continued)

*Primary Examiner* — Andre J Allen
(74) *Attorney, Agent, or Firm* — Dinsmore & Shohl LLP

(57) ABSTRACT

A sensor apparatus includes at least one substrate layer of an elastically deformable material, the substrate layer extending longitudinally between spaced apart ends thereof. A conductive layer is attached to and extends longitudinally between the spaced apart ends of the at least one substrate layer. The conductive layer includes an electrically conductive material adapted to form a strain gauge having an electrical resistance that varies based on deformation of the conductive layer in at least one direction.

20 Claims, 7 Drawing Sheets

Related U.S. Application Data continuation of application No. 16/910,740, filed on Jun. 24, 2020, now Pat. No. 11,576,612, which is a continuation of application No. 16/159,010, filed on Oct. 12, 2018, now Pat. No. 10,694,999.

(60) Provisional application No. 62/572,279, filed on Oct. 13, 2017.

(51) Int. Cl.
*A61B 5/024* (2006.01)
*A61B 5/026* (2006.01)
*G01L 9/00* (2006.01)
*G01L 9/04* (2006.01)
*G01L 9/06* (2006.01)

(52) U.S. Cl.
CPC ............ *A61B 5/026* (2013.01); *A61B 5/6876* (2013.01); *G01L 9/0052* (2013.01); *G01L 9/06* (2013.01); *A61B 2562/12* (2013.01)

(58) Field of Classification Search
CPC . G01L 19/06; G01L 19/0627; G01L 19/0681; G01L 27/002; G01L 9/00; G01L 9/0041; G01L 9/0044; G01L 11/04; G01L 19/0023; G01L 19/069; G01L 19/142; G01L 19/16; G01L 7/00; G01L 7/163; G01L 7/166; G01L 9/0047; G01L 9/12; G01L 11/02; G01L 13/00; G01L 15/00; G01L 19/003; G01L 19/0609; G01L 19/0672; G01L 19/083; G01L 19/10; G01L 19/148; G01L 27/005; G01L 7/08; G01L 7/082; G01L 9/0045; G01L 9/0048; G01L 9/006; G01L 9/007; G01L 9/0076; G01L 9/04; G01L 9/045; G01L 9/06; G01L 9/065; G01L 9/125; G01L 11/00; G01L 17/00; G01L 19/00; G01L 19/0015; G01L 19/0076; G01L 19/02; G01L 19/08; G01L 19/141; G01L 19/145; G01L 19/146; G01L 1/142; G01L 1/2262; G01L 1/246; G01L 21/12; G01L 23/16; G01L 27/007; G01L 7/04; G01L 7/063; G01L 7/084; G01L 7/086; G01L 7/16; G01L 9/0002; G01L 9/0007; G01L 9/0016; G01L 9/0019; G01L 9/0022; G01L 9/0027; G01L 9/0033; G01L 9/0039; G01L 9/005; G01L 9/0058; G01L 9/0077; G01L 9/0079; G01L 9/008; G01L 9/0092; G01L 9/0095; G01L 9/025; G01L 9/08; G01L 9/085; G01L 9/105; G01L 9/14; G01L 9/16
USPC .................................................... 73/700–756
See application file for complete search history.

(56) References Cited

U.S. PATENT DOCUMENTS

| | | | | |
|---|---|---|---|---|
| 2024/0023821 | A1* | 1/2024 | Majerus | A61B 5/0215 |
| 2025/0318739 | A1* | 10/2025 | Majerus | A61B 5/026 |

* cited by examiner

FLEXIBLE SENSOR APPARATUS AND METHOD OF MAKING SAME

CROSS-REFERENCE TO RELATED APPLICATION

The present application is a continuation application of U.S. patent application Ser. No. 18/108,808, filed Feb. 13, 2023, which is a continuation application of U.S. patent application Ser. No. 16/910,740, filed Jun. 24, 2020 (now U.S. Pat. No. 11,576,612), which is a continuation application of U.S. patent application Ser. No. 16/159,010, filed Oct. 12, 2018 (now U.S. Pat. No. 10,694,999), which claims the benefit of priority from U.S. Provisional Application No. 62/572,279, filed on Oct. 13, 2017, and entitled FLEXIBLE PULSATION SENSOR, the entireties of which are hereby incorporated herein by reference.

GOVERNMENT SUPPORT

This invention was made with government support under RX001968-01 awarded by U.S. Dept. of Veterans Affairs Rehabilitation Research and Development Service. The United States Government has certain rights in the invention.

TECHNICAL FIELD

This disclosure relates to a sensor apparatus and a method of making a sensor.

BACKGROUND

Sensors are used to monitor and measure a variety of biological conditions, such respiration, blood flow, and the like. As an example, an existing type of sensor may monitor a graft by placing the sensor at the graft in contact with the bloodstream. However, because use of such existing sensors contact with the bloodstream, such sensors may stimulate hypercellular processes to accelerate graft failure and/or or alter the graft mechanical structure. Accordingly, improved sensor designs are needed.

SUMMARY

In an example, a sensor apparatus includes at least one substrate layer of an elastically deformable material, the substrate layer extending longitudinally between spaced apart ends thereof. A conductive layer is attached to and extends longitudinally between the spaced apart ends of the at least one substrate layer. The conductive layer includes an electrically conductive material adapted to form a strain gauge having an electrical resistance that varies based on deformation of the conductive layer in at least one direction.

As another example, a method of making a sensor device includes providing a substrate layer of an elastically deformable material. The substrate layer extends longitudinally between spaced apart ends thereof. The method also includes forming a conductive layer on a surface of the substrate layer, the conductive layer extending longitudinally between the spaced apart ends of the at least one substrate layer. The conductive layer includes an electrically conductive material adapted to form a strain gauge having an electrical resistance that varies based on deformation of the conductive layer in at least one direction.

DETAILED DESCRIPTION

Figure 1:
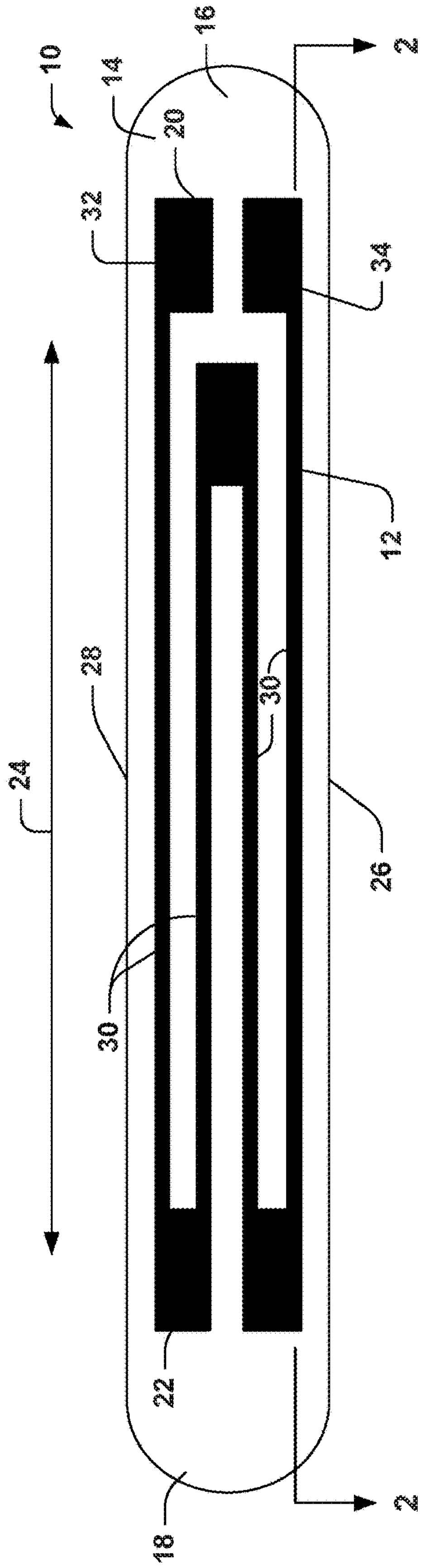
FIG. 1 depicts a top view of an example of a sensor apparatus.

This disclosure provides a sensor apparatus and a method for making the sensor apparatus. As an example, the sensor apparatus can include one or more substrate layers of an elastically deformable material and a conductive layer disposed over one of the substrate layers as to form a multi-layer sensor structure. For example, each layer can be fabricated as one or more webs or sheets that form a respective layer extending between spaced apart ends thereof. The conductive layer can be disposed over a given substrate layer. In an example, the conductive layer is sandwiched between at least two substrate layers. The conductive layer includes an electrically conductive material, such as by integrating the electrically conductive material into the elastically deformable material of the substrate layers. Thus, the conductive layer can exhibit compliance commensurate with the substrate layers.

The sensor apparatus, including the conductive layer, can be configured as a strain gauge having electrical resistance that varies based on deformation of the conductive layer in one or more directions. In an example, the sensor apparatus is constructed to have an anisotropic compliance, such as to be strain-sensitive along a predetermined direction while substantially less compliant and strain-insensitive along another direction that is transverse to its strain-sensitive direction.

For example, each of the layers of the sensor apparatus can be fabricated using an additive manufacturing process that deposits materials for each layer as a plurality of elongated strands extending in a longitudinal strand direction for each respective layer. Additionally, different layers of the sensor apparatus can include strands extending in different (e.g., transverse) directions. By spacing longitudinal strands apart from each other within a given layer, the resulting layer has multi-layer structure can be porous and thereby also exhibit a desired elasticity and compliance in each of the strand directions. The direction and spacing of strands within each layer thus can be configured to provide the sensor structure desired compliance in more than one direction. In some examples, the strand spacing can be less than a transverse direction than in a longitudinal direction so that the device stretches in a desired strain-sensitive direction.

As one example, the sensor apparatus may be mounted around a tubular structure that exhibits a change in a circumferential dimension (e.g., about 20% to about 100% change). Accordingly, the sensor structure is configured to have a compliance that is commensurate with or greater than the compliance of the tubular structure to which the sensor is attached. For example, the sensor can be attached around a tubular graft (e.g., a vascular graft) and the resistance of the conductive layer can be monitored over time to provide an indication of blood flow and/or efficacy of the graft. In an example, the conductive layer may be disposed directly onto the surface of the graft, such as by three-dimensional printing the conductive layer on an outer surface of the graft. The size and geometry of the sensor apparatus can be adapted according to a given application and surface where strain is to be measured in one or more directions.

Figure 2:
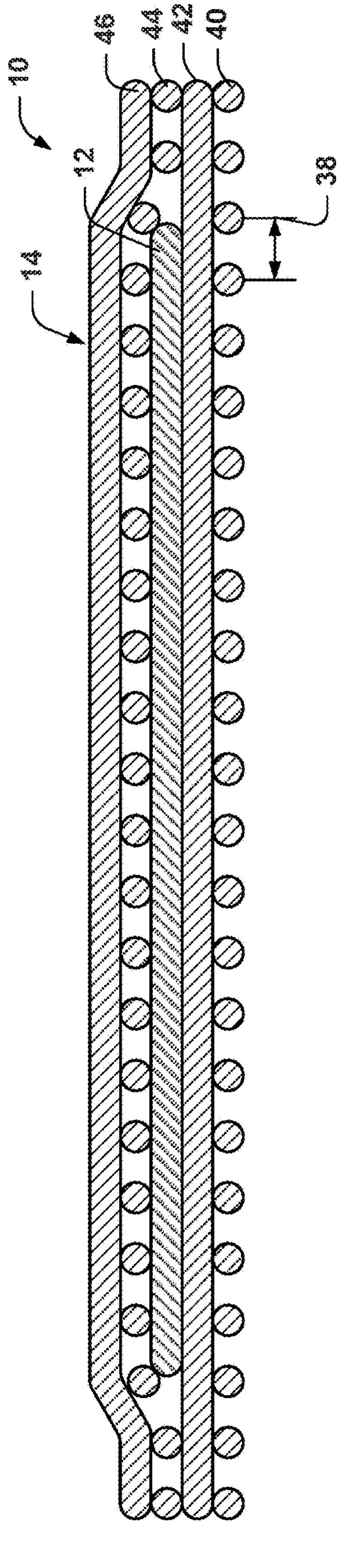
FIG. 2 is a side sectional view taken along line 2-2 in the example of FIG. 1.

Turning to the figures, FIGS. 1 and 2 depict an example of a sensor apparatus 10 that includes a conductive layer 12 that is attached to a substrate 14. The substrate 14 may include one or more layers of an elastically deformable and biocompatible material. As an example, each layer of the substrate 14 may be formed of a compliant polymer, such as a silicone (e.g., polydimethylsiloxane (PDMS)) or another similar compound. The conductive layer 12 may be formed by dispersing electrically conductive materials in a viscous polymer matrix. For example, the conductive materials may include micron or submicron conductive particles, such as carbon nanoparticles or graphene flakes. As one example, the conductive particles include a matrix of multi-walled carbon nanotubes (MWCNTs)) dispersed in PDMS, which are applied over a substrate 14 to form the conductive layer 12.

As shown in elongated sensor apparatus 10 of FIGS. 1 and 2, the substrate 14 extends between spaced apart ends 16 and 18. The conductive layer 12 likewise includes ends 20 and 22 that extend longitudinally between the ends 16 and 18 of the substrate 14. The longitudinal direction of the sensor apparatus 10 is demonstrated by arrow 24.

In an example, the sensor apparatus 10 can be configured to exhibit an isotropic compliance along a given direction with respect to a direction transverse to such direction. For instance, the sensor apparatus can be strain-sensitive along the direction 24 and exhibit compliance up to about 20% (or greater) in the strain sensitive direction (e.g., direction 24) such that the apparatus is elastically deformable along such direction, but is non-deformable in the transverse direction extending through side edges 26 and 28.

The conductive layer 12 includes an electrically conductive material. In an example, the electrically conductively material that may be integrated into the biocompatible material that is used to form the one or more layers of the substrate 14. The size and geometry of the strain gauge that is formed by the conductive layer 12 can vary according to application requirements. In a simple example, the conductive layer may be formed as one or more conductive strips extending longitudinally in the direction 24 between its spaced apart ends 20 and 22.

In another example, the strain gauge can be configured by a plurality of strips extending longitudinally in the direction 24 between the ends 20 and 22, such as an in a zig-zag or serpentine configuration. In one example, the conductive layer 12 is configured to include respective end portions adjacent to each of the ends 20 and 22 that are interconnected by longitudinally extending intermediate portions 30 (e.g., four intermediate portions shown in the example of FIG. 1). Different numbers of intermediate portions and patterns may be used in other examples. At one of the ends 20, the conductive layer includes contacts 32 and 34. The contacts 32 and 34 can be utilized to electrically connect the strain gauge to a measurement circuit, such as via wires or traces (see, e.g., FIG. 3).

FIG. 2 depicts a cross-sectional view of the sensor apparatus 10 taken along the line 2-2 in FIG. 1. As shown in FIG. 2, the conductive layer 12 is sandwiched between a plurality of substrate layers demonstrated at 40, 42, 44 and 46. In order to provide desired isotropic compliance along the given direction 24, each of the layers 12, 40, 42, 44 and 46 may formed of a plurality of parallel strands that are spaced apart from each other and arranged to extend in a direction that is parallel to or transverse to a strain-sensitive direction. As mentioned, the sensor apparatus 10 may be configured to have more than one strain sensitive direction, such as may include a longitudinal direction (e.g., direction 24) and a direction that is transverse to the longitudinal direction. The number of strands, the spacing between strands and the direction of strands in each respective layer 12, 40, 42, 44 and 46 thus will determine the compliance in each of the strand directions.

In the example of FIG. 2, the strands for layers 40 and 44 extend perpendicular to the sheet containing FIG. 2 (e.g., extending in a direction between edges 26 and 28 in FIG. 1). The strands in layers 12, 42 and 46 extend longitudinally with respect to the sheet corresponding to the direction 24 in FIG. 1. As mentioned, the space in between the strands 38 can be a configurable design parameter that is utilized to define the compliance for each of the layers, which collectively determines the overall compliance and deformability of the sensing apparatus 10.

As shown FIGS. 1 and 2, the strain gauge formed by the conductive layer 12 is encapsulated by the substrate 14. By way of further example, the conductive layer 12 is formed of strands extending in the longitudinal direction that is disposed over substrate layer 42 which also includes strands extending in the longitudinal direction. The combination of conductive layer 12 and substrate layer 42 are in turn sandwiched between layers formed by strands extending in a direction that is transverse to the longitudinal direction. Another layer 46 is disposed over the layer 44 and is formed by strands extended in the longitudinal direction. Other number of strands and different strand directions may be used in other examples.

Figure 3:
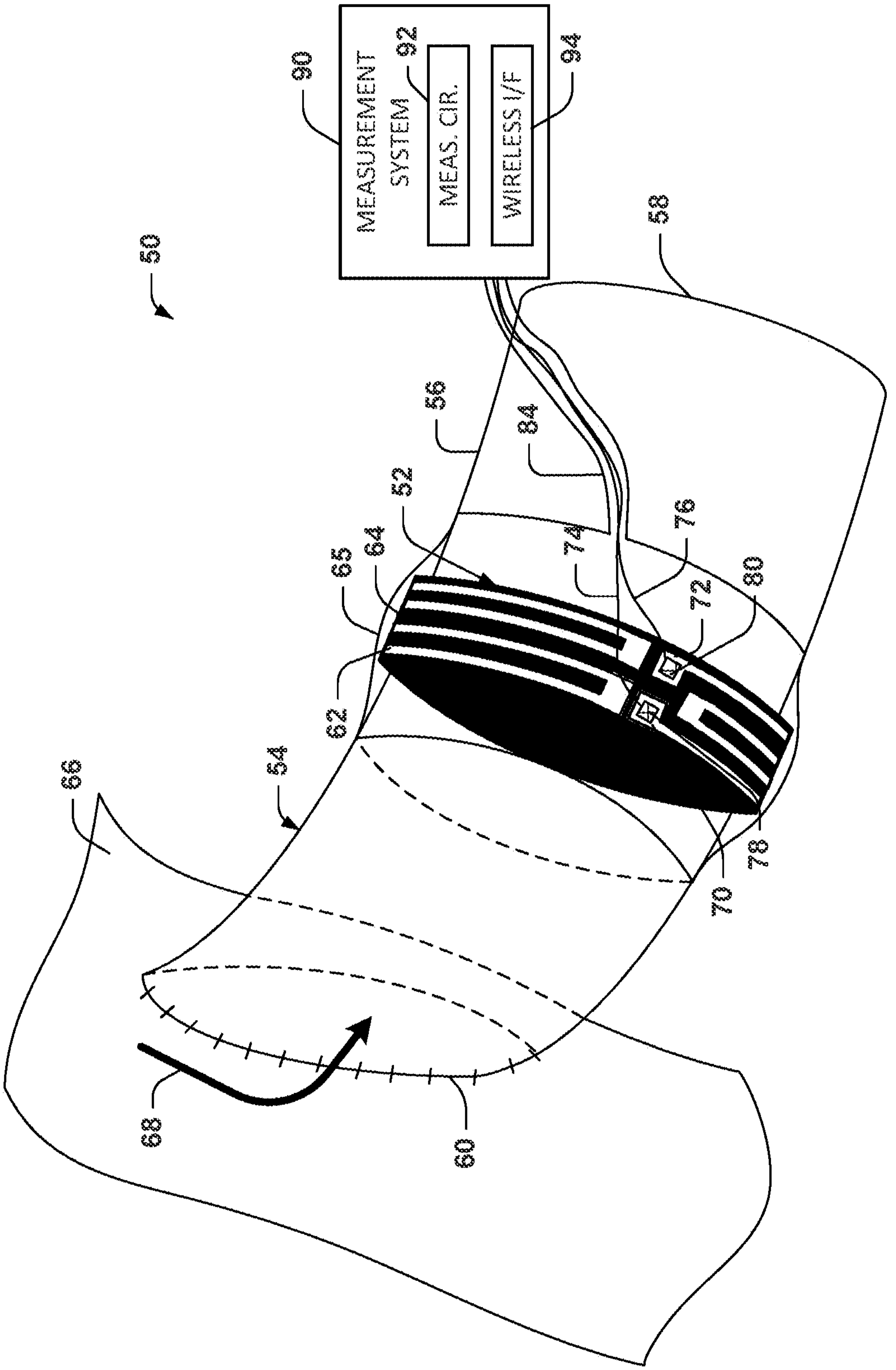
FIG. 3 depicts an example of a sensor system in which a sensor apparatus is mounted to a vascular graph.

FIG. 3 depicts an example of a sensor system 50 demonstrating a sensor apparatus 52 (e.g., sensor 10 of FIG. 1 or 2) mounted around a graft 54, which may be biological or synthetic tissue graft. For example, the graft is a hemodialysis access graft or other vascular graft. In this example, the end 60 of the graft 54 may be anastomosed to tissue 66 to provide for flow of blood through the graft in the direction 68. In other examples, one or more sensor apparatuses, as disclosed herein, may be applied to other surfaces (e.g., biological tissue or synthetic) for sensing deformation of such surface in one or more directions.

In the example of FIG. 3, the graft 54 includes a sidewall 56 that extends cylindrically between ends 58 and 60. In this example, the sensor apparatus 52 is mounted around the sidewall 56 as to circumscribe (partially or wholly) the graft 54. The sensor apparatus 52 may be mounted to the graft 54 such that a radially inner surface (e.g., bottom layer 40) of the sensor apparatus 52 approximates the outer diameter of the sidewall 56. As disclosed herein, the sensor apparatus is fabricated to have a compliance that is commensurate with or greater than the compliance of the sidewall 56 of the graft 54. In this way, deformation of the sidewall 56, such as occurs in the pulsation of blood flow therethrough, results in corresponding deformation of the sensor apparatus 52.

The sensor apparatus 52 can be configured as disclosed with respect to FIGS. 1 and 2. For example, the sensor apparatus 52 is configured as a strain gauge that includes an electrically conductive layer 62 mounted between two or more substrate layers 64. In an example, the conductive layer is formed of a piezoresistive elastomer, such as a conductive PDMS or other material disclosed herein. The sensor apparatus 52 thus is sufficiently compliant to deform in a radial or circumferential direction corresponding to sensor strain (e.g., from about 0% to about 20% strain) in response to pulsatile blood flow through the graft that causes graft wall motion. Such deformation causes a change in electrical resistance in the conductive layer 62 that can be measured over time.

By way of further example, the circumference of the sensor apparatus 52 that engages the graft sidewall 56 corresponds to a length of the apparatus that can be wrapped around or otherwise mounted to the sidewall (e.g., by sutures, an adhesive or the attachment mechanism). Since the sensor apparatus 52 is fixed externally to the graft 54, the sensor apparatus can monitor graft motion based on the electrical resistance of the conductive layer, which changes based on deformation. As mentioned, the substrate and conductive layers may be anisotropically compliant to enable radial or circumferential deformation but prevent deformation in the axial dimension (along its width). As a result, the deformation causes a change in resistance that correlates to flow rate and/pressure through the graft 56. As a result, the sensor apparatus 52 can enable detection of graft dysfunction without adversely affecting blood flow through the graft. In other examples, alternatively or additionally, one or more sensor apparatus 52 can be attached to the sidewall 56 of other tissue to monitor other tissue function. A compliant covering 65 of a compliant biocompatible material further may applied over the sensor apparatus and a portion of the adjacent sidewall 56.

In this example, electrical conductors (e.g., wires) 74 and 76 are coupled to electrical contacts (terminals) 70 and 72 of the sensor apparatus 52. The contacts may be provided at ends of the electrical trace formed by the conductive layer 62. For example, electrical conductors 74 and 76 can be coupled to the contacts 70 and 72 by flexible connecting members 78 and 80. As an example, flexible connecting members 78 and 80 may be in the form of a compliant mesh or other flexible pad material that can be fixed to ends of the conductive wires 74 and 76 and fixed to the contacts 70 and 72 (e.g., by an adhesive or solder). The conductive wires 74 and 76 can extend from the contacts 70 and 72 through a biocompatible cover end 84 to connect the sensor apparatus 52 with a corresponding measurement system 90.

By way of example, the measurement system 90 includes circuitry 92 configured to measure the electrical resistance between the contacts 70 and 72 over time. As disclosed herein, the electrical resistance may be measured in response to application of an AC signal (e.g., pulses). As mentioned, the electrical resistance of the conductive layer 62 varies as a function of its length, corresponding to circumferential strain of the graft 54 and sensor apparatus. (e.g., operating as a strain gauge). The electrical resistance of the sensor apparatus 52 may be determined to provide measurement data that is stored in memory of the measurement system (not show). In other examples, additional processing of the determined electrical resistance may be implemented by the measurement system 90 (e.g., by a processor) to provide processed measurement data, such as representing graft wall motion, pressure and/or flow through the site where the sensor apparatus 52 is mounted.

The measurement system 90 may also include a wireless interface to communicate measurement data and operating parameters to a remote location. In an example, the wireless communication interface 94 is adapted to transmit measurement data wirelessly from the measurement system 90 to a remote location. The wireless interface 94 may be implemented as an inductive communications link or according another wireless technology, such as 802.11x Wi-Fi, Bluetooth, ZigBee, cellular or the like that can communicate data to a remote device. The remote device may be smart phone, server or other wireless receiver.

As a further example, the measurement system 90 or a remote device may be configured to monitor graft wall motion based on the measurement data. In response to detecting a decrease in graft wall motion below an established threshold based on the measurement data, which can be calibrated for a given graft implant, an occurrence of a dysfunction may be determined, such as an occlusion, stenosis or other physiological condition. The measurement system or remote device thus may generate an alert in response to determining the dysfunction. The alert may be communicated to the patient and/or one or more caregivers. In this way, additional testing may be performed to determine if an intervention may be required to avoid graft failure and extend graft patency.

Figure 4:
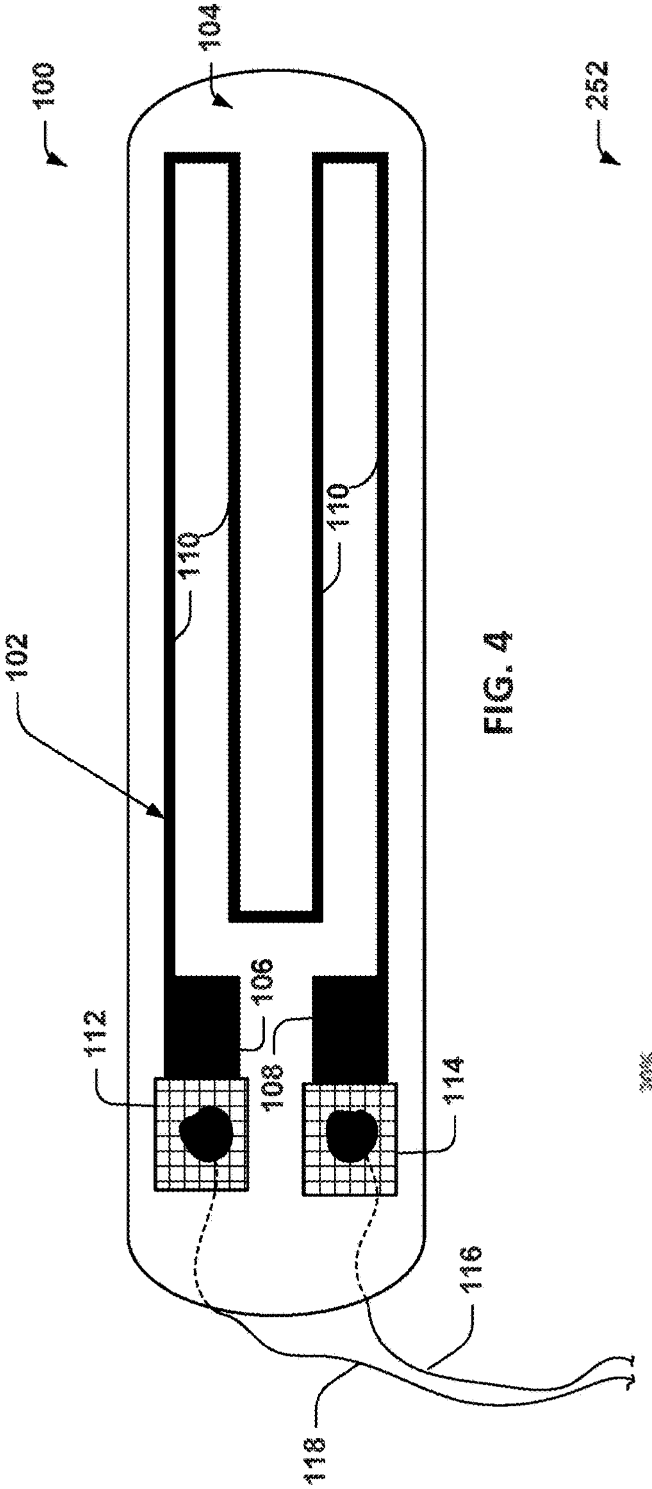
FIG. 4 depicts an example of a sensor apparatus with electrical wires coupled to contacts of the apparatus.

FIG. 4 depicts an example of another sensor apparatus 100. The sensor apparatus includes an electrically conductive layer 102 in the form of a strain gauge that is mounted to, such as being encapsulated within, a substrate 104. As mentioned, the substrate 104 may include a plurality of layers of a biocompatible elastically deformable material, such as PDMS. The conductive layer 102 may be a conductive PDMS material. The conductive layer 102 and biocompatible substrate 104 may be implemented such as disclosed herein. In the example of FIG. 4, the conductive layer 102 includes electrical contact portions 106 and 108 at ends of a conductive trace. The conductive trace includes intermediate longitudinally extending portions 110 that form a serpentine or zig-zag pattern between the contact portions 106 and 108.

Additionally, the sensor apparatus 100 includes mesh support members 112 and 114 to connect corresponding ends of electrically conductive wires 116 and 118 with the electrical contacts 106 and 108, respectively. For example, the electrically conductive wires (e.g., wires 74, 76) can extend through vias or other holes formed through the layers and through the corresponding conductive contacts 106 and 108 and through holes in the mesh support members 112 and 114. The mesh support members 112 and 114 may be formed of stainless steel material, an electrically conductive polymer or other material to facilitate electrically connecting ends of the wires 116 and 116 to the conductive layer 102. The ends of the conductive wires 116 and 118 that extend transversely through the layers of the sensor apparatus 100 can be fixed to the mesh support 112 and 114 by an electrically conductive material, such as solder, an adhesive, mechanical fitting (e.g., friction fitting or clamp) or the like.

As an example the sensor apparatus 100 is a rectangular cuboid composed of a central CPDMS strain gauge layer sandwiched between two or more layers of thixotropic structured PDMS. The example sensor apparatus in the example of FIG. 4 includes a conductive layer configured as a strain gauge having 4 longitudinally extending strips (e.g., 20×1.5 mm and 0.23 mm thick) and enlarged contact pads 32 and 34. Each of the strips 110 were spaced 1.5 mm apart. The outer 2 layers of structured PDMS each measured about 0.46 mm thick with rectangular pores (e.g., 80 μm×160 μm pores). The pores reduce the rigidity of the structured PDMS layers to improve the strain sensitivity.

Figure 5:
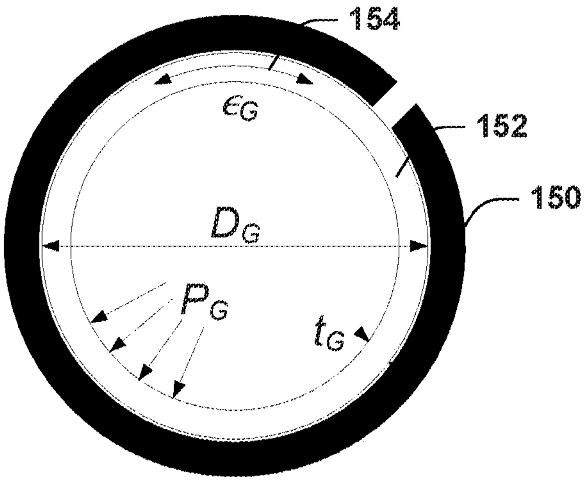
FIG. 5 depicts a side view of a sensor apparatus mounted around a graph.

By way of further example, FIG. 5 depicts a sectional view of an example flexible sensor 150 (e.g., in the form of a cylindrical sensor body) positioned circumferentially around a cylindrical graft 152. In this example, the circumferential direction 154 provides for expansion and contraction radially of the combined graft and sensor structure. The deformation of the cylindrical body of the sensor 150 results from pressure, demonstrated as $P_G$, according to the thickness of the graft 152 and its corresponding compliance. As disclosed herein, the sensor apparatus 150 is mounted circumferentially about the graft 152. The sensor apparatus 150 has a compliance that exceeds (it is more compliant than) the graft, which itself is compliant to enable its radial deformation in response to pulsatile flow of fluid through the graft. Thus, radial deformation of the graft 152 is transferred to and results in corresponding deformation of the sensor apparatus 150. The resulting deformation along the circumferential dimension of the sensor apparatus 150 can be sensed and measured by a measurement system (e.g., measurement system 90 of FIG. 3).

Figure 6:
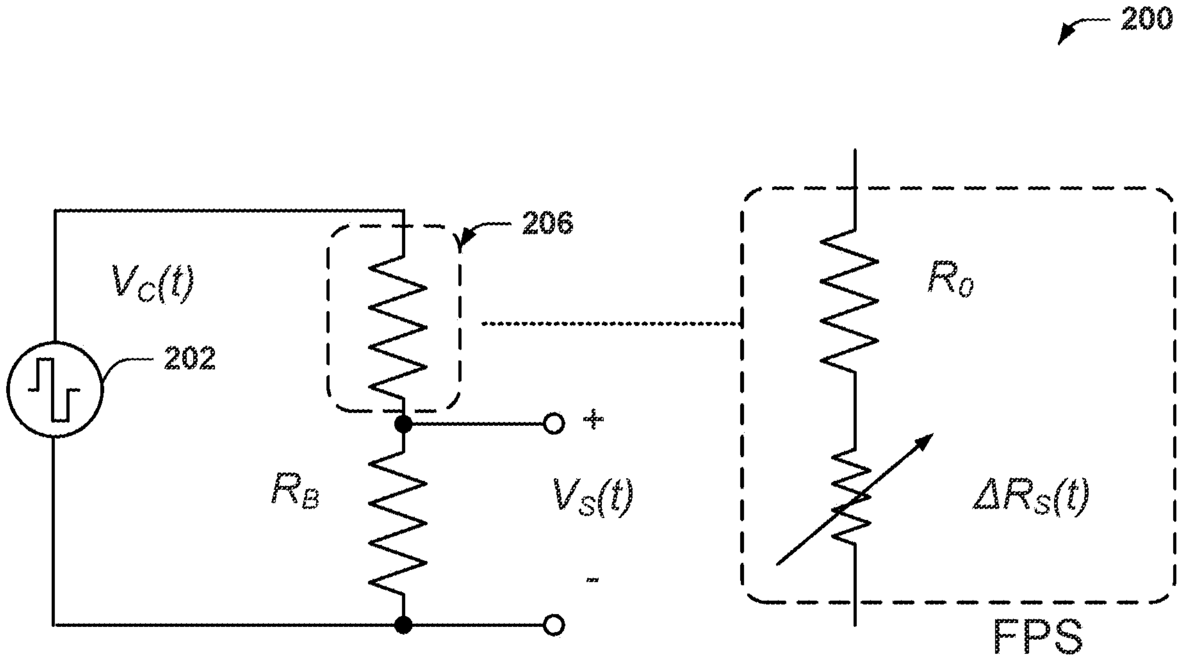
FIG. 6 depicts an example of part of the sensing circuit that can be used to measure resistance of the sensor apparatus.

As an example, the measurement circuitry (e.g., circuitry 92) of the measurement system may be implemented to include circuitry 200, such as shown in FIG. 6. In the example of FIG. 6, the measurement circuitry 200 includes a voltage source 202, which may be configured to supply an AC voltage, demonstrated as $V_C$ (t). The voltage $V_C$ (t) is thus applied to a resistance network, such as the resistive divider that includes a known resistance $R_B$ and a variable resistance 206. The variable resistance 206 that models the resistance of the conductive layer (e.g., between corresponding electrical contacts thereof) that changes over time in response to deformation thereof.

For example, the resistance 206 may include a nominal resistance $R_0$ of the sensor apparatus 150 in series with a variable resistance, demonstrated as $\Delta R_S(t)$. The variable resistance $\Delta R_S(t)$ represents the time-variant sensor resistance exhibited by the conductive layer under periodic pulsatile flow. That is, in response to changes in the diameter $D_G$ of the sensor apparatus, which corresponds to expansion and contraction in size along the circumferential strain-sensitive direction, a resulting sensor voltage $V_S(t)$ varies over time. For example, the sense voltage $V_S(t)$ may be obtained across the resistor $R_B$, as shown in FIG. 6. Thus, by monitoring the voltage $V_S(t)$ across the resistor $R_B$ over time, an indication of the strain that is applied to the sensor apparatus may also be monitored over time. As disclosed herein, the variable resistance $\Delta R_S$ (t) exhibited by the conductive layer of the sensor can vary depending upon the geometry and compliance of the sensor in different directions.

As a further example with reference to FIGS. 5 and 6, the following mathematically describes transduction mechanics linking graft pressure and flow to change in resistance of the sensor apparatus 150 via mechanical strain. In this example, the model assumes that the sensor apparatus 150 is the same circumference as the graft 152 and is mechanically linked such that the sensor and graft distension are equal under pressurized flow. For example, it can be assumed, via the Poiseuille equation that graft flow $Q_G$ and pressure $P_G$ are linearly related by a factor η, i.e. $\eta Q_G = P_G$.

For a cylindrical graft, circumferential stress $\sigma_\theta$ is approximated by Barlow's equation and related to the graft Young's modulus $E_G$ by:

$$E_G = \frac{\sigma_\theta}{\epsilon_G} = \frac{P_G D_G}{2t_G} \cdot \frac{1}{\epsilon_G}, \tag{1}$$

where $\in_G$ is the circumferential strain in the graft, and $D_G$ and $t_G$ are the graft 154 diameter and thickness, respectively. Because the sensor apparatus 150 is more flexible than the graft, it can be reasonably assumed that the graft's modulus and thickness are mechanically dominant. The change in circumferential length ΔL can be calculated through circumferential strain $\in_G = \Delta L / L_0$):

$$\Delta L = \frac{\pi P_G D_G^2}{2t_G \cdot E_G}. \tag{2}$$

Under a pressure $P_G$, the sensor strain $\in_S$ is approximately:

$$\epsilon_S \cong \epsilon_G = \frac{P_G D_G}{2t_G \cdot E_G}, \tag{3}$$

which is the same as (1) with the assumption $\in_S \cong \in_S$. To first order, $\in_S$ is therefore proportional to graft pressure and flow. For a sensor apparatus coupled in a half bridge with $R_B$ (FIG. 6), $\in_S$ is the nominal sensor resistance and $\Delta R_S$ (t) represents the time-variant sensor resistance under periodic pulsatile flow, such as mentioned above. The resistance $\Delta R_S$ (t) can be derived using a strain sensor gauge factor (GF) conversion, such as follows:

$$\Delta R_S(t) = P_G(t) \frac{R_0 D_G}{2t_G E_G} \cdot GF. \tag{4}$$

The change in sensor resistance is linked to graft flow through the relation $\eta Q_G(t) = P_G(t)$. If $R_B$ is chosen as $R_B = R_0$, the flow-dependent sensor output is given by:

$$V_S(t) = V_C(t) \frac{1}{2 + \eta Q_G(t) \frac{D_G}{2t_G E_G} \cdot GF} \tag{5}$$

If all time-invariant factors (relating to sensor geometry and material properties) are grouped into a single term $\gamma_{FPS}$, the sensor output signal is approximately:

$$V_S(t) = V_C(t) \cdot (2 + \gamma_{FPS} Q_G(t))^{-1} \tag{6}$$

In some examples, to mitigate memristive effects and to reduce the effect of 1/f noise, $V_C$ (t) can be an AC carrier, i.e. a square wave. Equation (6) shows that the FPS output in these conditions is an AM-modulated waveform with modulation index $h = \max(\gamma_{FPS} Q_G(t)) / \max(V_C(t))$.

Figure 7:
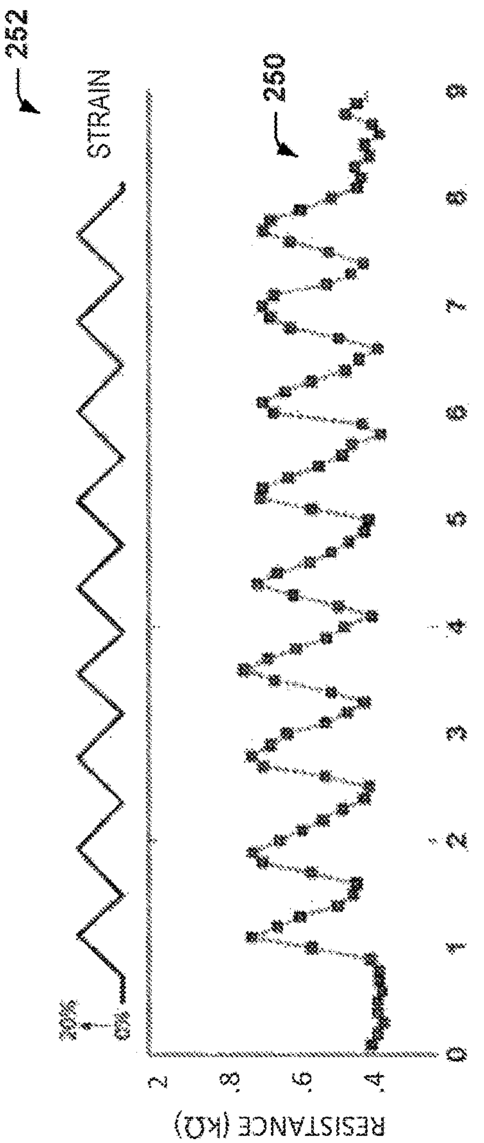
FIG. 7 is a graph demonstrating resistance of the function of time demonstrating an example of cyclical deformation of the sensor apparatus.

An example of resistance sampled over time in response to changes in the strain of a sensor apparatus is shown in FIG. 7. In this example, the strain of the sensor apparatus may vary between 0 and 20% over time such as in response to the pulsation of blood through a graft to which the sensor apparatus is applied such as shown in FIG. 3. In the example of FIG. 7, the resistance varies over time to provide a corresponding measure of the strain which as described herein correlates to arterial pressure.

Figure 8A:
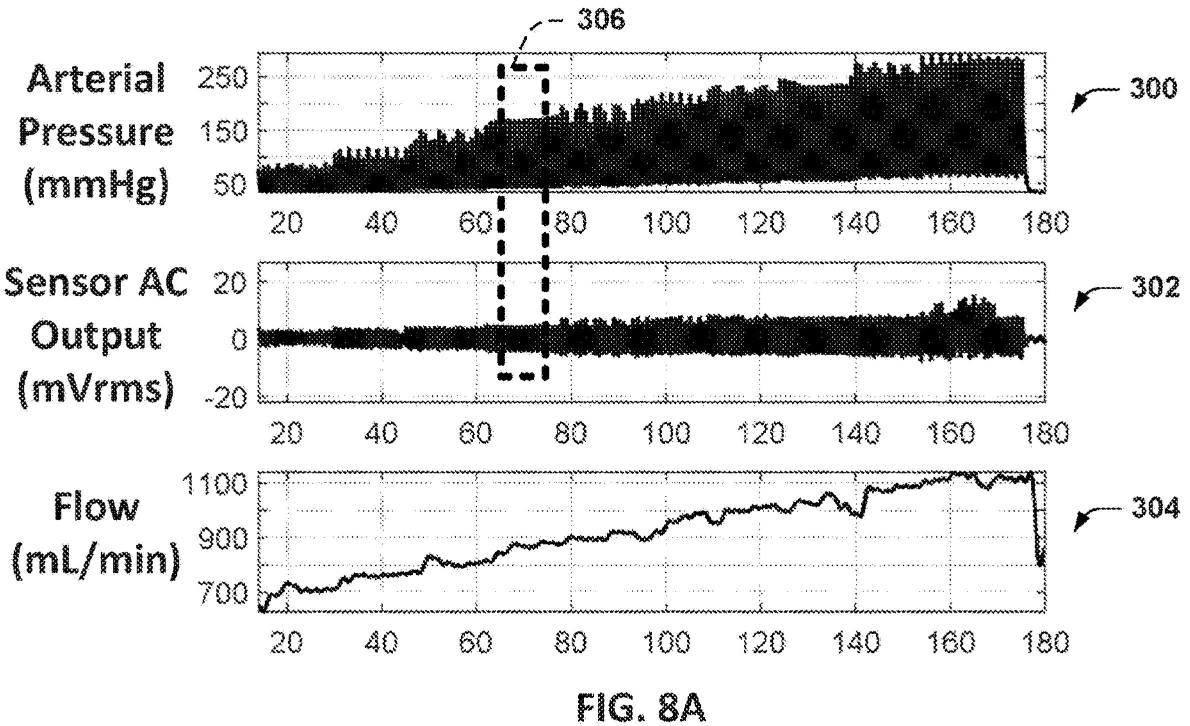
FIGS. 8A and 8B are graphs demonstrating a relationship between a sensor apparatus and arterial pressure over a range of different flow rates.
Figure 8B:
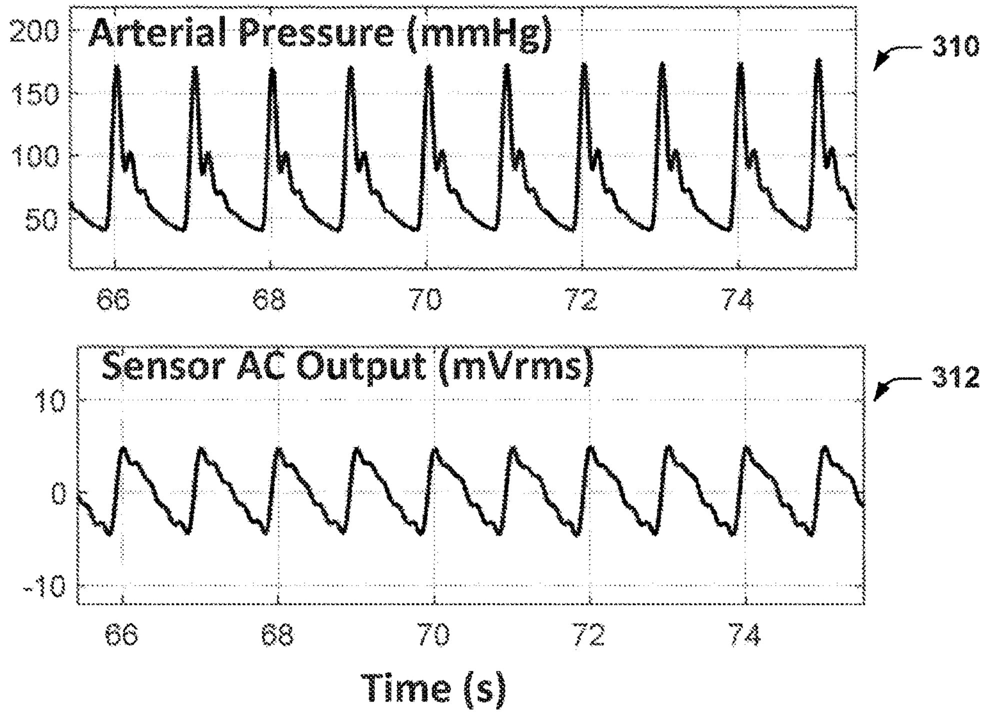

As a further example, FIGS. 8A and 8B demonstrate plots 300, 302, and 304 demonstrating arterial pressure, sensor output and flow pressure, respectively. As demonstrated in the portion of the plots 300 and 302 by dotted line 306 an enlarged view of the arterial pressure and sensor output are shown at 310 and 312 in FIG. 8B. In this way, the sensor output (e.g., $V_S(t)$ in FIG. 6), provided in mVrms, is shown to track the arterial pressure.

Figure 9:
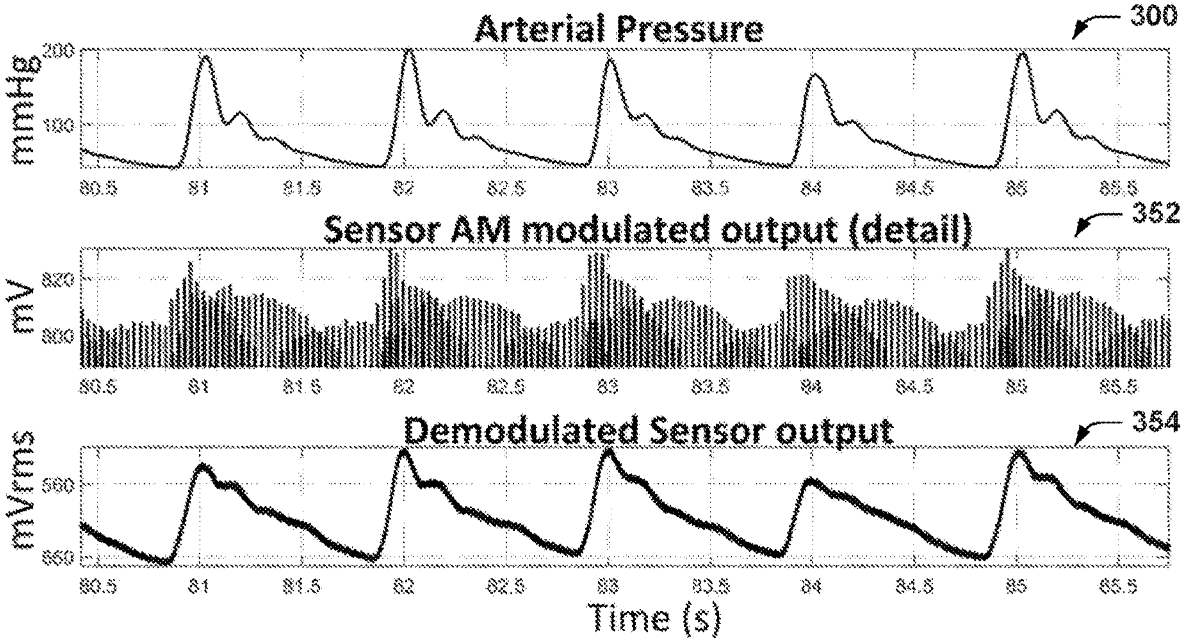
FIG. 9 is a graph depicting a demodulated sensor output, a modulated sensor output and arterial pressure.

The relationship between arterial pressure and sensor output is further demonstrated in FIG. 9. For example, FIG. 9 includes plots of arterial pressure 350, sensor AC output (unmodulated) 352 and demodulated sensor output 354 over time. Thus it is shown that the demodulated sensor output provides a sensor signal that is amplitude modulated based on flow through the graft. Due to the correlation between flow and pressure, the sensor apparatus thus can measure both properties. The measurement system (e.g., system 90) can include a filter (e.g., a moving root-mean-square (RMS) filter with 10 Hz cutoff) to demodulate the sensor output 352 and provide the demodulated sensor signal 354. Envelope or synchronous demodulation may also be implemented by the measurement system.

Figure 10:
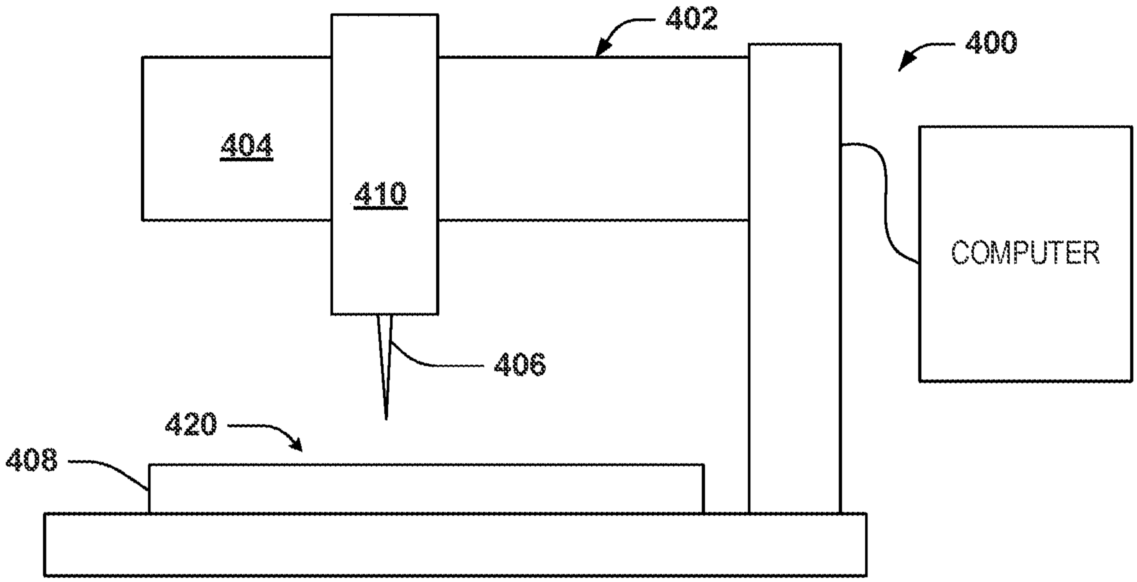
FIG. 10 depicts an example of an additive manufacturing system configured to make sensor apparatuses.

FIG. 10 depicts an example of a system 400 for fabricating one or more sensor apparatuses (e.g., sensor 10, 52, 100, 150). In the example of FIG. 10, the system 400 is an additive manufacturing system. The additive manufacturing system can include a 3-D printer 402 configured to form respective layers of the multi-layer sensor apparatus, such as by extruding strands of material in transverse directions such as disclosed herein (See e.g., FIG. 2). The printer 402 includes a print head 404 that includes a dispensing tip such as a syringe (or other nozzle) 406 to apply uncured material on a stage 408 for each of the layers of the sensor apparatus. The stage 408 may be heated to cure the applied materials. As one example, the system 400 may be implemented as an EnvisionTec 3D Bio-plotter system. The system 400 can 3D print the sensor apparatus from a CAD model of a sensor apparatus (e.g., stored as data and instructions in a non-transitory machine-readable medium) that is transferred to the printer from a computer or other device storing data of the CAD model.

In an example, the system 400 may move the syringe tip 406 longitudinally and in transverse directions to apply strands of the material in different (e.g., orthogonal directions), such as strands in a direction along the length of a sensing apparatus in a direction transverse to the longitudinal direction. The system 400 can be configured to control the spacing between individuals strands in each layer to control the compliance of the resulting sensor in each strand direction. By imposing spacing between strands in the respective layers, the sensor body can be porous, which can enhance its compliance. Additionally, by controlling the spacing as to be different in different strand directions an isomorphic strain sensitivity can be provided. For example, the sensor apparatus can be strain-sensitive in a direction with a spacing that is greater than the strand spacing in transverse direction to such strain-sensitive direction. As one example, the strand spacing in a transverse axis may be about 15% to about 65% less than the longitudinal strain-sensitive axis so that the sensor body stretches in the strain-sensitive direction but not along the transverse direction.

As disclosed herein, according to one example, the substrate layers can be a biocompatible compliant material, such as PDMS. The conductive layer can be a conductive biocompatible compliant material, such as conductive PDMS. The system 400 thus can include one or more containers (e.g., cartridges) 410 to hold the materials for the substrate layers and conductive layer. In an example, the conductive layer may be formed by dispersing conductive particles (e.g., MWCNTs) in PDMS to form conductive PDMS. For example, the conductive layer may be formed of a ratio of MWCNT/PDMS (e.g., about 1%-12%, such as about 2%-6%).

As a further example, CPDMS is produced by gently grinding MWCNT granules can be ground in a ceramic mortar and sieving to 0.1 mm to produce the CPDMS. MWCNTs can be evenly dispersed in toluene (e.g., at 10 wt % and sonicated for 30 min (e.g., using a Qsonica Q500 probe, 500 W, 20 kHz, approximately 30% duty cycle). Next, an elastomer base and curing agent (e.g., Sylgard 184 PDMS available from Dow Corning) may be added to the MWCNT dispersion. Fumed silica can be added (e.g., at about 0.45 wt %) to help stabilize the mixture when printing. The MWCNT-PDMS-toluene mixture may be magnetically stirred at room temperature to evaporate the toluene. The mixture may be transferred to a vacuum desiccator and evaporated to below 3% residual toluene by weight, then transferred to a syringe barrel (e.g., nozzle 406) for 3D Bio-plotting by the system 400. As mentioned, other types of electrically conductive particles may be used in other examples.

Figure 11:
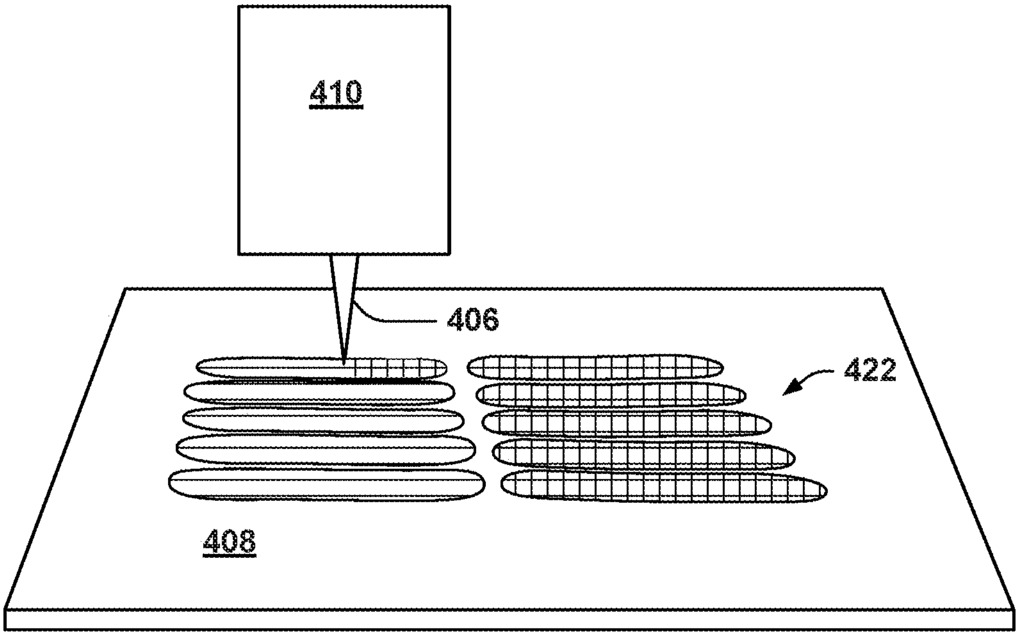
FIG. 11 depicts an enlarged view demonstrating part of the system of FIG. 10 showing the plurality of apparatuses being manufactured.

FIG. 11 shows an enlarged view of print area 420 of the system 400 of FIG. 10. For example, the print area 420 resides on a planar surface of the heated stage 408 to facilitate flow of the material and curing thereof in the desired configuration. Corresponding printed structures 422 thus are formed on a print area 420 of the stage 408, such as shown in FIG. 11. Thus in FIG. 11 a plurality of printed sensor structures 420 are shown. In some examples, the conductive layer can be disposed (e.g., 3D printed) directly onto a surface of graft to form an integrated sensor-graft structure. One or more layers of the substrate material (e.g., PDMS) may be printed over the conductive layer to encapsulate and hold the sensor over the surface of the graft. In other examples, the sensor apparatus may be mounted to a surface of a graft or other surface where strain is to be monitored.

In view of the foregoing, 3D structures can be fabricated using additive manufacturing, enabling flexible pulsation sensors for vascular graft flow- and pressure sensing. Since the sensor apparatus can be fabricated from a 3D printer, its size, geometry and compliance parameters may be customized for a given application.

Figure 12:
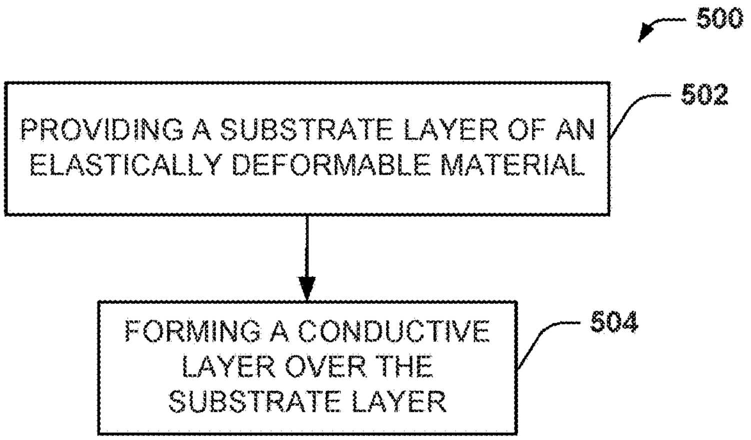
FIG. 12 is a flow diagram depicting an example method of making a sensor apparatus.

FIG. 12 is a flow diagram depicts an example of a method that can be implemented for making one or more sensor devices (e.g., 10, 52, 100, 150 and 422). In an example, the method may be performed by the system 400 of FIGS. 10 and 11, although other equipment may be used in other examples.

At 502, the method includes providing a substrate layer (e.g., 12, 54, 102) of an elastically deformable. For example, the elastically deformable may also be a biocompatible material such as PDMS. The substrate layer extends longitudinally between spaced apart ends thereof. The size and geometry of the substrate layer and the resulting sensor device can vary according to application requirements. In an example, the substrate layer may be formed by additive manufacturing, such as 3D printing.

At 504, a conductive layer is formed onto a surface of the substrate layer, extending longitudinally between the spaced apart ends of the at least one substrate layer. The conductive layer includes an electrically conductive material such that the conductive layer forms a strain gauge having an electrical resistance that is adapted to vary based on deformation of the conductive layer in at least one direction. For example, the electrically conductive material includes carbon particles integrated within PDMS (e.g., in a mixture), such as disclosed herein. The conductive layer may be formed by additive manufacturing, such as 3D printing over the substrate layer. In one example, a graft or other structure may itself be the substrate that is provided at 502, and the conductive layer may be applied directly onto the graft or other structure (e.g., by 3D printing).

In some examples, one or more other substrate layer over the conductive layer such that the conductive layer is sandwiched between at least two substrate layers. In this way, the plurality of substrate layers and the conductive layer are configured to exhibit anisotropic compliance a given direction and direction transverse to the given direction. The method further may include mounting the sensor apparatus to a surface of a target site where strain measurements are to be made. The surface may include a biological tissue surface, such as a vessel wall, surface of an organ (e.g., stomach, liver, heart, skin or the like). The resulting strain measurements can be used for monitoring the surface where the sensor apparatus (or apparatuses) are attached and/or for monitoring a condition internal to the surface (e.g., blood flow, muscle contractions, etc.). In a particular example, the sensor apparatus may be mounted around a cylindrical sidewall of an annular graft, such as disclosed herein, to measure graft function as well as blood flood characteristics (e.g., flow rate and/or pressure).

What have been described above are examples. It is, of course, not possible to describe every conceivable combination of structural and functional features or methodologies, but one of ordinary skill in the art will recognize that many further combinations and permutations are possible.

Unless defined otherwise, all technical and scientific terms used herein have the same meaning as is commonly understood by one of skill in the art to which the present disclosure pertains.

As used herein, the term "and/or" can include any and all combinations of one or more of the associated listed items.

As used herein, phrases such as "between X and Y" and "between about X and Y" can be interpreted to include X and Y.

It will be understood that when an element is referred to as being "on," "attached" to, "connected" to, "coupled" with, "contacting," etc., another element, it can be directly on, attached to, connected to, coupled with or contacting the other element or intervening elements may also be present.

As used herein, the phrase "at least one of X and Y" can be interpreted to include X, Y, or a combination of X and Y. For example, if an element is described as having at least one of X and Y, the element may, at a particular time, include X, Y, or a combination of X and Y, the selection of which could vary from time to time. In contrast, the phrase "at least one of X" can be interpreted to include one or more Xs.

As used herein, the term "includes" means includes but not limited to, the term "including" means including but not limited to. Additionally, where the disclosure or claims recite "a," "an," "a first," or "another" element, or the equivalent thereof, it should be interpreted to include one or more than one such element, neither requiring nor excluding two or more such elements.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. A "predetermined" status may be determined at any time before the structures being manipulated actually reach that status, the "predetermination" being made as late as immediately before the structure achieves the predetermined status (e.g., on the fly during fabrication).

The term "substantially" is used herein to indicate a quality that is largely, but not necessarily wholly, that which is specified, allowing some amount of variation (e.g., +/−5%). Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one example or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this application, including the appended claims.

Accordingly, the disclosure is intended to embrace all such alterations, modifications, and variations that fall within the scope of this application, including the appended claims.

What is claimed is:

1. A sensor apparatus comprising:

at least one substrate layer of an elastically deformable material, the substrate layer extending longitudinally between spaced apart ends thereof; and a conductive layer disposed over the at least one substrate layer, the conductive layer including an electrically conductive material adapted to form a strain gauge having anistropic or isotropic compliance, wherein the sensor apparatus is configured to be wrapped at least partially around a tubular structure.

2. The sensor apparatus of claim 1, further comprising a measurement system connected to the sensor apparatus, the measurement system including circuitry configured to measure the electrical resistance between a first electrical contact and a second electrical contact of the sensor apparatus.

3. The sensor apparatus of claim 2, wherein the measured electrical resistance comprises measurement data that is stored in a memory of the measurement system.

4. The sensor apparatus of claim 3, wherein the measurement system comprises a processor adapted to process the measurement data to provide processed measurement data, such as pressure and/or blood flow through a site where the sensor apparatus is mounted.

5. The sensor apparatus of claim 1, wherein the conductive layer of the sensor apparatus forms a piezoresistive strain gauge.

6. The sensor apparatus of claim 5, wherein the piezoresistive strain gauge has an electrical resistance between respective ends of the conductive layer that varies based on deformation of the conductive layer in at least a longitudinal direction thereof.

7. The sensor apparatus of claim 1, wherein the at least one substrate layer further comprises a plurality of substrate layers of the elastically deformable material, the conductive layer being sandwiched between at least two substrate layers.

8. The sensor apparatus of claim 7, wherein the elastically deformable material of each of the substrate layers comprises polydimethylsiloxane (PDMS), and the electrically conductive material of the conductive layer comprises electrically conductive particles integrated with PDMS.

9. The sensor apparatus of claim 7, wherein the plurality of substrate layers and the conductive layer are configured to exhibit anisotropic compliance to enable deformation along a given direction and inhibit deformation along a direction transverse to the given direction.

10. The sensor apparatus of claim 9, wherein each of the substrate layers and the conductive layer includes a plurality of substantially-parallel strands of its material arranged to extend in a direction that is parallel or transverse to the given direction, the direction of the strands and spacing between strands in each respective layer defining the anisotropic compliance of the apparatus along respective strand directions.

11. The sensor apparatus of claim 9, wherein the given direction is longitudinal or radial.

12. A method comprising the steps of:

advancing the sensor apparatus of claim 1 into a patient;

mounting the sensor apparatus to a biological surface of the patient; and generating, by the sensor apparatus, one or more strain measurements associated with the biological surface.

13. The method of claim 12, wherein the biological surface is a vessel wall.

14. The method of claim 12, further comprising the step of monitoring a condition internal to the biological surface.

15. The method of claim 14, wherein the monitoring is performed by a measurement system of the sensor apparatus.

16. A sensor apparatus comprising:

at least one substrate layer of an elastically deformable material, the substrate layer extending longitudinally between spaced apart ends thereof; and a conductive layer disposed over the at least one substrate layer, the conductive layer including an electrically conductive material adapted to form a strain gauge having anistropic or isotropic compliance, wherein the conductive layer of the sensor apparatus forms a piezoresistive strain gauge.

17. The sensor apparatus of claim 16, wherein the piezoresistive strain gauge has an electrical resistance between respective ends of the conductive layer that varies based on deformation of the conductive layer in at least a longitudinal direction thereof.

18. The sensor apparatus of claim 16, wherein the at least one substrate layer further comprises a plurality of substrate layers of the elastically deformable material, the conductive layer being sandwiched between at least two substrate layers.

19. The sensor apparatus of claim 18, wherein the elastically deformable material of each of the substrate layers comprises polydimethylsiloxane (PDMS), and the electrically conductive material of the conductive layer comprises electrically conductive particles integrated with PDMS.

20. The sensor apparatus of claim 18, wherein the plurality of substrate layers and the conductive layer are configured to exhibit anisotropic compliance to enable deformation along a given direction and inhibit deformation along a direction transverse to the given direction.

* * * * *